United States Patent
Liska et al.

(10) Patent No.: US 8,022,155 B2
(45) Date of Patent: Sep. 20, 2011

(54) POLYMERIZED MOLDED BODY

(75) Inventors: Robert Liska, Vienna (AT); Monika Schuster, Vienna (AT); Jürgen Stampfl, Vienna (AT); Heinrich Gruber, Vienna (AT); Franz Varga, Mauerbach (AT)

(73) Assignee: Technische Universitat Wien, Vienna (AT)

( * ) Notice: Subject to any disclaimer, the term of this patent is extended or adjusted under 35 U.S.C. 154(b) by 228 days.

(21) Appl. No.: 11/918,513

(22) PCT Filed: Apr. 10, 2006

(86) PCT No.: PCT/AT2006/000143
§ 371 (c)(1),
(2), (4) Date: Oct. 15, 2007

(87) PCT Pub. No.: WO2006/108202
PCT Pub. Date: Oct. 19, 2006

(65) Prior Publication Data
US 2008/0287565 A1    Nov. 20, 2008

(30) Foreign Application Priority Data
Apr. 14, 2005 (AT) ............................. A 626/2005

(51) Int. Cl.
*C08H 1/00* (2006.01)
*A61F 2/01* (2006.01)
(52) U.S. Cl. ............... 526/238.1; 523/115; 526/199; 527/201
(58) Field of Classification Search ............... 523/113, 523/114, 115, 116, 118; 106/35; 527/200–207; 526/238.1
See application file for complete search history.

(56) References Cited

U.S. PATENT DOCUMENTS

| | | | | |
|---|---|---|---|---|
| 4,663,409 A | | 5/1987 | Friends et al. | 526/242 |
| 4,979,989 A | * | 12/1990 | Ridoux | 106/35 |
| 5,415,864 A | * | 5/1995 | Kopecek et al. | 424/436 |
| 5,621,119 A | * | 4/1997 | Podszun et al. | 549/229 |
| 5,733,994 A | * | 3/1998 | Koepff et al. | 527/207 |
| 5,837,752 A | * | 11/1998 | Shastri et al. | 523/116 |
| 5,856,120 A | * | 1/1999 | Fedorov et al. | 435/68.1 |
| 6,281,265 B1 | * | 8/2001 | Montgomery et al. | 523/122 |
| 6,455,608 B1 | * | 9/2002 | Jia et al. | 523/115 |
| 6,458,386 B1 | * | 10/2002 | Schacht et al. | 424/488 |
| 7,053,051 B2 | * | 5/2006 | Hendriks et al. | 530/350 |
| 2002/0193516 A1 | * | 12/2002 | Bucevschi et al. | 525/54.1 |
| 2003/0114552 A1 | * | 6/2003 | Schacht | 523/113 |
| 2004/0133143 A1 | * | 7/2004 | Burton et al. | 602/58 |
| 2004/0234574 A9 | * | 11/2004 | Sawhney et al. | 424/426 |
| 2006/0223776 A1 | * | 10/2006 | Frechet et al. | 514/44 |
| 2010/0017972 A1 | * | 1/2010 | Sartore et al. | 8/436 |

FOREIGN PATENT DOCUMENTS
EP    1 142 596    10/2001

OTHER PUBLICATIONS
Zimmermann et al. Biomaterials 23 (2002) 2127-2134.*

* cited by examiner

*Primary Examiner* — Mark Eashoo
*Assistant Examiner* — Michael Salvitti
(74) *Attorney, Agent, or Firm* — Drinker Biddle & Reath LLP

(57) ABSTRACT

The invention relates to polymerizable compositions which comprise 10-80% by weight of a reactive diluent based on acrylic acid or methacrylic acid derivatives, and 10-50% by weight of a monomer of the indicated chemical formula which is liquid or which can be dissolved in the formulation. The formula may contain amino acid residues or peptide sequences, especially such that are specific of the collagen. These structural elements allow the enzymatic degradation of the polymers of the inventive composition.

19 Claims, No Drawings

POLYMERIZED MOLDED BODY

The invention relates to radiation curable, biocompatible and bioresorbable compositions and their use in molding processes for producing polymeric support materials for bone replacement.

For quite some time, metal implants in the form of screws, pins, nails or plates have been used for healing bone fractures, with the disadvantage that a second surgery is necessary for removing these fixation parts. Subsequently, screws, pins and nails made of polyglycolic acid, polylactic acid, and their copolymers have been used for fixing bone fractures, on the one hand because of their mechanical properties coming close to those of bone, on the other hand because these implants are degraded in the body and thus avoid a second surgery.

When bone tumors have to be removed, however, there remains more extensive damage that has to be filled. This requires a material serving as support for a short period of time, i.e. for the time the organism requires to rebuild the bone. In addition, this material should also support the natural healing process and be completely resorbed by the body after a certain period of time. Therefore, this material must not only be biocompatible and biodegradable, but also be particularly suitable for the adherence and proliferation of bone cells (osteoblasts). Furthermore, such replacement material should have a structure similar to that of natural bone, i.e. it should be a porous composite with a cellular structure, if possible.

There are two basic possibilities to create a porous bone structure. On the one hand, a substance that produces pores when cured may be introduced into a liquid monomer formulation. This may be a foaming agent or a solid material, such as sodium chloride or sugar, which may be dissolved out afterwards.

In WO 98/20893, for example, a method is described in which monomer mixtures are cured in the presence of sugar cubes in a silicone mold, whereafter the sugar is dissolved out with water. In such a method, the pore size and the inner geometry may only be regulated within certain statistical limits, so that it is not possible to create defined cellular structures.

A more useful method for producing implants is the rapid prototyping (RP) method wherein a monomer formulation is photopolymerized in layers to achieve a desired, "tailor-made" 3D cellular structure. This allows not only the production of any irregular shape, like those usually found in bone defects, but also results in a resolution close to the pore diameters of bone (100 to 500 μm). However, conventional biopolymers as they have been used for medical applications, such as poly(α-hydroxy acids), cannot be produced by means of RP methods because they are not accessible from photopolymerizable monomers. Photocrosslinkable formulations resulting in biodegradable and biocompatible polymers have occasionally been described in literature.

In WO 03/002490 A2 biomaterials based on poly(propylene fumarate) that are cross-linkable with diethyl fumarate are claimed. These mixtures may be used either for producing prefabricated implants by means of molding methods, or as injectable formulations which are cured in vivo by photopolymerization.

Since such formulations always contain a prefabricated polymer, i.e. poly(propylene fumarate), adjustment of an appropriate viscosity is only possible with high contents of diethyl fumarate, which leads to weakly crosslinked and thus mechanically rather instable molded articles, though. A targeted production of porous structures is thus not possible, and the rise in temperature caused by the photopolymerization also constitutes a problem for in vivo applications.

The poly(propylene fumarate)/diethylene fumarate system has also been used in a stereolithographic method (M. Cooke, J. P. Fisher, D. Dean, C. Rimnac, A. Mikos, Journal of Biomedical Materials Research—Part B Applied Biomaterials, vol. 64, no. 2, pp. 65-69 (Feb. 15, 2003)). With this method, the production of a prototype molded article was possible, which was not porous, though. Furthermore, the mechanical stability of the molded articles, having an elastic modulus of approx. 200 MPa, did not meet the mechanical requirements for bone replacement materials since natural bone has an elastic modulus of more than 2000 MPa. Here, too, the authors refer to problems regarding viscosity of the polymer/monomer mixture, which leads to the production of molded articles that do not exactly correspond to the CAD model. A high content of diethyl fumarate results in a reduction of viscosity, but also inhibits the crosslinking procedure. A low content leads to high crosslinking, which, however, entails a reduction of bioresorbability. This system thus allows only limited regulation of the outer and inner morphology of the implants, even by using stereolithography. Another problem is the well-known low polymerization rate of fumarates.

W. Matsuda et al. (T. Matsuda, M. Mizutani, S. Arnold, Macromolecules 2000, 33. 795-800, M. Mizutani, T. Matsuda, Journal of Biomedical Materials Research, vol. 61, no. 1, pp. 53-60 (2002)) describe photocurable biodegradable polymers based on poly(ε-caprolactone-co-trimethylene carbonate). By means of ring-opening copolymerization of ε-caprolactone with trimethylene carbonate, branched aliphatic polyesters were produced, into which terminal coumarin groups were then introduced. Irradiation with ultraviolet light leads to photodimerization of the terminal groups and thus crosslinks the polyesters. In addition to problems regarding the adjustment of viscosity, which are also encountered in this case, crosslinking only occurs via the terminal groups. This does not only lead to very low crosslinking rates, but also to polymers with low crosslinking densities, which is unfavorable for the mechanical properties of the molded article, as is shown by low elastic moduli of 40 MPa at the most.

The polymerization rate could be raised by introducing terminal acrylate groups into the same branched polyesters, but this does not solve the other problems mentioned (M. Mizutani, T. Matsuda, Journal of Biomedical Materials Research 62, 395 (2002)).

U.S. Pat. No. 6,083,524 claims macromonomers with acrylate end-groups with a polyethylene glycol central segment extended with blocks of poly(lactic acid) or poly(glycolic acid). These were used to produce biodegradable hydrogels via photopolymerization. Disadvantages of these products are their low mechanical strength and especially their poor cell adhesion. This is attributed to a high content of polyethylene glycol which is known to show resistance to protein adsorption and cell adhesion (A. S. Sawhney, C. P. Pathak, J. A. Hubbell, Macromolecules 26, 581-587 (1993)). Similar macromonomers with a diethylene glycol central unit and blocks of oligo(lactic acid) or oligo(caprolactone) resulted in materials with a somewhat better adhesion of osteoblasts (K. A. Davis, J. A. Burdick, K. S. Anseth, Biomaterials 24, 2485-2495 (2003)). In both cases, however, the highly viscous or solid monomers are not usable in rapid prototyping methods.

A general disadvantage of such aliphatic polyesters based on glycolic acid or lactones is that bonds are comparatively labile to hydrolysis, i.e. are relatively quickly degraded in aqueous environments. This degradation is hydrolytic and cannot be controlled by the autocatalytic character. Furthermore, this bone replacement material disintegrates faster than new bone tissue can be formed. In addition, high acid concentrations may occur, which creates an environment that may lead to uncontrolled cell death and thus to necrotic tissue changes. Therefore, purely enzymatic degradation would by preferable, i.e. with a biomaterial stimulating growth of bone cells (osteoconductive), so that these cells also produce enzymes for degrading the polymer. In this way, the body's own cells may to a certain extent regulate degradation of the implanted plastic. Basically, polymers built via hydrolytically more stable amide bonds are more useful.

Thus, the use of hydrogels based on gelatin and polyethylene glycol as biomaterials is known, wherein the hydrogels are produced by radical copolymerization of Jeffamine® bis-methacrylamides with methacrylamide-substituted gelatin (J. Zimmermann, K. Bittner, B. Stark, R. Mülhaupt, Biomaterials 23, 2127-2134 (2002)). These hydrogels are characterized by good cell adhesion and proliferation. Due to the use of polymeric units (e.g. Jeffamine® bis-methacrylamide having an Mn of approx. 2000, gelatin with Mn of approx. 3000), however, these hydrogels have very low mechanical strengths, with moduli, depending on the water contents of the gels, ranging from 240 to 480 kPa, i.e. some orders of magnitude below those required for bone replacement materials. Furthermore, these viscous formulations are only water-soluble and not suitable for rapid prototyping methods.

Special hydrogel compositions are claimed in EP 1,142, 596 A1 for the production of therapeutically active implants consisting of crosslinkable prepolymers (macromers) and biologically active peptides or proteins. Further optional additives mentioned are inorganic materials and/or vinyl monomers. A crucial factor during use is the mixture's appropriate viscosity to allow molding by hand, by means of syringes or by means of other surgical instruments. Prepolymers consisting of flexible aliphatic backbone chains are used for this purpose, which form wide-meshed networks of prepolymers after polymerization. After molding, the pasty material is introduced into the corresponding defective site and cured in situ using redox initiators or photoinitiators at temperatures below 40° C.

WO 98/55161 A1 describes wound dressing materials based on crosslinked methacrylamide-modified gelatin or copolymers thereof with methacryl-modified polysaccharides (e.g. dextrane or xanthan). These hydrogel films are by nature soft materials with good absorptive capacities for aqueous media since this is a requirement for wound covering and dressings.

US 2004/110439 describes biocompatible protein fibers and crosslinked fibers or fabrics for medical applications, which optionally comprise living cells. The fibers are produced on the basis of polymerizable derivatives of proteins, for example elastin, collagen or gelatin, or polymerizable derivatives of peptide sequences that are characteristic for these proteins. The fibers are produced by electrospinning, followed by photochemical crosslinking via polymerizable groups by aid of photoinitiators. If necessary, e.g. when spinning collagen, water-soluble polymers (polyethylene oxide) are added. This increases the fibers' mechanical stiffness, albeit only to a rather limited extent. For collagen PEO fibers, for example, elastic moduli in the range of 8 to 12 MPa are reported.

In WO 91/08242 A1 graft copolymers are described that are produced by grafting mixtures of peptides, proteins, vinyl monomers and crosslinkers on insoluble finished polymers, such as cellophane or polyethylene terephthalate, by means of gamma radiation. This procedure results in flexible films with biocompatible surfaces, which may be molded into implants for blood vessel replacements.

Better mechanical properties were achieved with biomaterials based on lysine urethane dimethacrylate, which were obtained by photopolymerization in the presence of calcium hydroxylapatite (E. Müh, J. Zimmermann, U. Kneser, J. Marquardt, R. Mülhaupt, B. Stark, Biomaterials 23, 2849-2854 (2002)). These materials show good cell compatibility and adhesion, but the monomer mixture is solid, may only be polymerized after melting, and is consequently not suitable for rapid prototyping methods. It is not possible to produce mechanically stable molded articles, arbitrary geometrical configurations and cellular structures.

The invention aims to provide a radiation curable composition which may be used for the production of—especially cellular or porous—molded articles with high mechanical strength, similar to that of natural bone, by means of rapid prototyping methods and which may be used as bioresorbable support materials for bone replacement. The compositions must be liquid, biocompatible, non-toxic and highly reactive. In addition to showing biocompatibility, bioresorbability and sufficient mechanical stability, the polymer produced by the RP procedure must contain structural elements guaranteeing good adhesion of osteoblasts, also called bone-forming cells. Furthermore, sufficient hydrolytic stability is necessary, so that enzymatic degradation induced by bone cells is favored.

It has been found that this object may be achieved with liquid, radiation curable formulations containing not only reactive diluents, photoinitiators and fillers, but also monomers with amino acid radicals and peptide sequences, respectively, especially such being specific for collagen. On the one hand, these structural elements provide good adhesion of osteoblasts, on the other hand, they serve as a substrate for the enzymatic apparatus of the cells, so that enzymes cleaving the polymer are increasingly produced. Bioresorption thus primarily occurs via enzymatic degradation.

The object of the invention is a polymerization-curable composition containing
a) 10 to 80% by weight of a reactive diluent based on acrylic acid or methacrylic acid derivatives,
b) 10 to 50% by weight of a liquid monomer, or a monomer soluble in the formulation (the composition), of the general formula

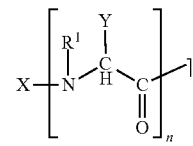

wherein n is an integer between 1 and 100,
X represents hydrogen or $R^3$ or (C=O)—$R^3$, with $R^3$ being a linear or branched alkyl radical of 1 to 20 C atoms, optionally having one or more intervening oxygen atoms or ester groups, or the radical

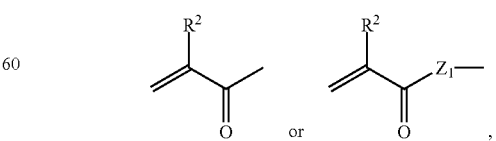

with $R^2$ being H or —$CH_3$,
wherein $Z_1$ is —O—$(CH_2)_x$—CO—, —O—$(CH_2$—$CH_2$—O$)_x$—$CH_2$—CO—,     —O—$(CH_2$—$CH_2$—O$)_x$—CO—

CH$_2$—CH$_2$—CO—, —O—(CH$_2$—CH$_2$—O)$_x$—OC—CH=CH—CO— —O—CH$_2$—CH(OH)—CH$_2$—, or —O—(CH$_2$—CH$_2$—O)$_x$—CH$_2$—CH(OH)—CH$_2$—, with x being 1 to 20, the radicals Y independently represent hydrogen, —CH$_3$, —CH$_2$—CH(CH$_3$)$_2$, —CH(CH$_3$)—CH$_2$—CH$_3$, —CH$_2$—COT, —CH$_2$—CH$_2$—COT, —CH$_2$—OX, —(CH$_2$)$_4$—NHX, —(CH$_2$)$_3$—NH—C(=NH)—NH$_2$—, —CH$_2$SX, —CH(OX)—CH$_3$, —CH$_2$—CH$_2$—S—CH$_3$, —CH$_2$—C$_6$H$_5$, —CH$_2$—C$_6$H$_4$—OX, —CH$_2$—CONH$_2$, —CH$_2$—CH$_2$—CONH$_2$,

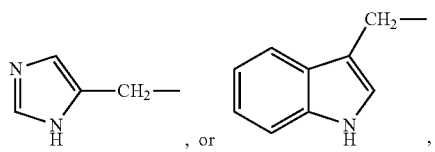
, or wherein X has the same meaning as above,
R$^1$ represents hydrogen or R$^3$ or (C=O)—R$^3$, with R$^3$ having the same meaning as above, or R$^1$ together with Y represent the radical —(CH$_2$)$_3$— or —CH$_2$—CH(OX)—CH$_2$—, wherein X has the same meaning as above,
T represents the group —OH or OR$^3$ or the radical

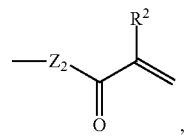

with R$^2$ being H or —CH$_3$,
wherein Z$_2$ is —O—(CH$_2$)$_x$—O—, —O—(CH$_2$—CH$_2$—O)$_x$—, —O—CH$_2$—CH(OH)—CH$_2$—O—, or —O—CH$_2$—CH(OH)—CH$_2$—O—(CH$_2$—CH$_2$—O)$_x$—, with x being 1 to 20, with the proviso that at least one radical X, Y or T contains the group

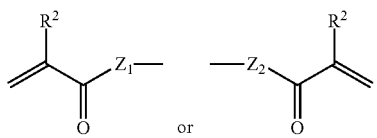

In a preferred embodiment, the composition is a composition which is curable (polymerizable) with ultraviolet or visible light, comprising as the component b) 10 to 50% by weight of a liquid monomer, or a monomer soluble in the formulation, of the general formula

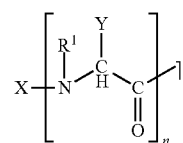

wherein n is an integer between 1 and 100,

X represents hydrogen, the radical

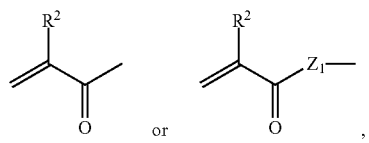

with R$^2$ being H or —CH$_3$,
wherein Z$_1$ is —O—(CH$_2$)$_x$—CO—, —O—(CH$_2$—CH$_2$—O)$_x$—CH$_2$—CO—, —O—CH$_2$—CH(OH)—CH$_2$—, or —O—(CH$_2$—CH$_2$—O)$_x$—CH$_2$—CH(OH)—CH$_2$—, with x being 1 to 20,
the radicals Y independently represent hydrogen, —CH$_3$, —CH$_2$—CH(CH$_3$)$_2$, —CH(CH$_3$)—CH$_2$—CH$_3$, —CH$_2$—COT, —CH$_2$—CH$_2$—COT, —CH$_2$—OX, —(CH$_2$)$_4$—NHX, —(CH$_2$)$_3$—NH—C(=NH)—NH$_2$—, —CH$_2$SX, —CH(OX)—CH$_3$, —CH$_2$—CH$_2$—S—CH$_3$, —CH$_2$—C$_6$H$_5$, —CH$_2$—C$_6$H$_4$—OX, —CH$_2$—CONH$_2$, —CH$_2$—CH$_2$—CONH$_2$,

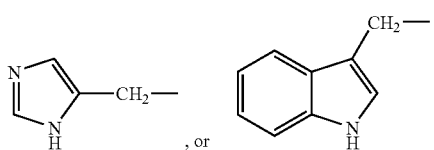
, or wherein X has the same meaning as above,
R$^1$ represents hydrogen or R$^1$ together with Y represent the radical —(CH$_2$)$_3$— or —CH$_2$—CH(OX)—CH$_2$—, wherein X has the same meaning as above,
T represents the group —OH or the radical

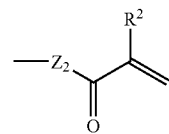

with R$^2$ being H or —CH$_3$,
wherein Z$_2$ is —O—(CH$_2$)$_x$—O—, —O—(CH$_2$—CH$_2$—O)$_x$—, —O—CH$_2$—CH(OH)—CH$_2$—O—, or —O—CH$_2$—CH(OH)—CH$_2$—O—(CH$_2$—CH$_2$—O)$_x$—, with x being 1 to 20,
with the proviso that at least one radical X, Y or T contains the group

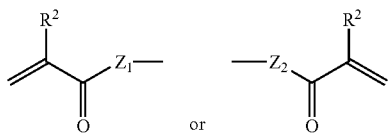

Preferably, the composition contains 0 to 60% of a filler or solvent.
Preferably, 0.01 to 5% by weight of at least one initiator, optionally 0 to 5% by weight of a co-initiator and/or 0 to 10% by weight of one or more additives such as stabilizers, UV absorbers, viscosity modifiers, solvents, are added.
According to the invention, as the reactive diluents any known mono-, di- or multifunctional acrylic or methacrylic esters and amides and/or any mixture thereof may be used, for example acrylic acid, methacrylic acid, hydroxyethyl acrylate, hexanediol diacrylate, polyethylene glycol diacrylate, pentaerythritol triacrylate, dimethylacrylamide, diethylacrylamide, polylactic acid-block-polyethylene glycol-block-polylactic acid diacrylate.

Liquid derivatives, e.g. N,N-diisopropylacrylamide, acrylic acid 2-(butylcarbamoyloxy)ethyl ester, polyethylene glycol diacrylate, and trimethylolpropane triacrylate, are preferred.

The monomers listed under b) are specific (meth)acryloylated amino acids, peptides or proteins. According to the invention, these may be substituted at one or both of the terminal groups and/or at pendant groups of respective reactive amino acid units such as lysine, serine, tyrosine, aspartic acid or glutamic acid radicals. Such monomers are known from the literature (E. Schacht, WO 98/55161 (1998) (J. Zimmermann, K. Bittner, B. Stark, R. Mühlhaupt, Biomaterials 23, 2127-2134 (2002)), but may also be produced by reacting peptides with reactive (meth)acrylic acid derivatives such as (meth)acrylic acid chloride, anhydride or glycidyl ester. The peptides used for these reactions may be mixtures obtained by hydrolysis of naturally occurring proteins, for example gelatin, keratin, fibrin or casein, or peptide mixtures from rice, soybeans, wheat, potatoes, hens' eggs, meat or fish. According to the invention, (meth)acryloylated peptides containing collagen-specific amino acid units (e.g. glycine, arginine, aspartic acid, glutamic acid, alanine, proline, hydroxylysine, or hydroxyproline) as well as (meth)acryloylated gelatin hydrolysates having molecular weights of up to 10.000 are preferred. Particularly preferred according to the invention are (meth)acryloylated peptides which comprise sequences containing special receptors for cell adhesion (e.g. arginine-glycine-aspartic acid, the so-called RGD sequence, cf. D. L. Hern, J. A. Hubbell, Journal of Biomedical Materials, Research Part A 39, 266-276 (1998)).

According to the invention, the polymerizable (meth)acryloyl radicals may also be attached to the peptide via a spacer. Suitable reagents for the reaction are: 12-methacryloyloxy-dodecanoic acid anhydride, (14-methyl-13-oxo-3,6,9,12-tetraoxapentadec-14-ene-1-yl)butane-1,4-dioic acid monoester (EP 324,455 A2) or commercially available acryloxypolyethylene glycol-N-hydroxysuccinimide.

In addition to conventional thermal initiators, photoinitiators are particularly preferred. Useful photoinitiators are any radical-forming type I and type II initiators (see "Photoinitiators for free radical polymerization" by J. Crivello and K. Dietliker, Wiley/SITA London). Examples include benzilketals, benzoins, hydroxalkylphenones, aminoalkylphenones, acylphosphine oxides, bisacylphosphine oxides, titanocenes. Type II initiators such as benzophenones, diketones, thioxanthones as well as ketocoumarins are used with suitable co-initiators. These are generally tertiary amines such as 4-dimethylaminobenzoic acid ethylester (DMAB), triethanolamine or dimethylethanolamine.

According to the invention, campherquinone/DMAB, 2-hydroxy-1-[4-(2-hydroxyethoxy)phenyl]-2-methyl-1-propanone (Irgacure 2959) or phenyl-bis(2,4,6-trimethylbenzoyl)phosphine oxide (Irgacure 819) are particularly useful.

The fillers used may be any known biocompatible and bioinert organic polymer or inorganic material. These may be soluble or dispersed in the form of powders, fibers or the like in the liquid monomer mixtures. Examples include polyvinylpyrrolidone, polyvinyl alcohol, casein, keratin, gelatin, cellulose ester and ether, chitosan, starch derivatives, hyaluronic acid derivatives, polyesters based on poly-α-hydroxy acids, poly-ε-caprolactone, poly(propylene fumarates), polycarbonates, polyanhydrids, polyphosphazenes, aluminium oxide, zirconium oxide or Ti (Ta, Nb) alloys. Particularly preferred according to the invention are hydroxyapatite, tricalcium phosphate, bone meal, algipor, polyethylene glycol, polyester based on lactic acid and glycolic acid, keratin fibers, and fibrin adhesive.

In a further aspect, the present invention relates to the use of the composition for producing polymerizates and to a method for producing polymerizates by polymerization of the composition. Thermal initiators or photoinitiators may be used for polymerization.

Preferably, the polymerizate is a molded article, particularly one formed either by polymerization of the composition in a mold or by "rapid prototyping" (lithographic or stereolithographic rapid prototyping).

Preferably, the components of the composition are dissolved in organic solvents comprising a water content of <10%, preferably <1%, most preferably <0.1% (in % by weight, in some cases a fluid component may act as solvent).

In a further aspect, the present invention relates to molded articles consisting of the polymerizable composition, having an E-modulus of more than 500 MPa. Such molded articles are obtainable with the method described.

Preferably, the molded article has an E-modulus of more than 500 MPa, more preferably more than 1000 MPa, even more preferably more than 1500 MPa, still more preferably more than 2000 MPa, most preferably more than 5000 MPa or more than 10000 MPa.

The elastic modulus (also called Young's modulus) is a characteristic value of materials, describing the correlation between stress and strain during deformation of a solid body with linear elastic behavior. The elastic modulus is abbreviated E-modulus. The more resistance a material shows against deformation, the higher the elastic modulus' value. Thus, a material having a high elastic modulus is stiff, while a material having a low elastic modulus is yielding. The elastic modulus is defined as the slope of the curve in the stress-strain diagram during application of monoaxial stress within the linear elasticity portion.

Hardness is, among other factors, determined by the composition, which is preferably contained in anhydrous organic solvents, which avoids swelling or shrinkage due to water. Nor is any water generated during polymerization of the selected components of the composition. (Depending on the desired hardness, moisture may be acceptable in a minor amount.) In particular, the composition contains <10%, preferably <1%, most preferably <0.1%, of water (in % per weight). In particular, the components b) are not soluble in water (in some cases heterogeneous dispersion is admissible), but (homogeneously) soluble in organic solvents.

By producing molded articles for the use as bone replacement it is possible to produce articles having mechanical properties which are amazingly similar to those of bone material. An E-modulus of the molded article below 500 MPa is unfavorable because such an article is too rubber-like (compared to bone). Good values are between 1500 and 5000 MPa, the best would be around 10000 MPa, which corresponds to the value of natural bone. Such a high value is preferably achieved by additional use of fillers.

Macromeric structures such as those described by Anseth (Biomaterials 2003: 2485) or published in the EP 1,142,596 A1, only achieve a modulus of 500 MPa. Bismethacrylates of polyorthoesters merely have a modulus of approximately 40 MPa (M. Kellomaki, J. Heller, P. Tormala, Processing and properties of two different poly(ortho esters), Journal of Materials Science: Materials in Medicine 11(6), 345-355 (2000)), PEG-lactide-bismethacrylate of approximately 8 to 17 MPa (D. Cohn, A. Hotovely-Salomon, Biodegradable multiblock PEO/PLA thermoplastic elastomers: molecular design and properties, Polymer 46(7), 2068-2075 (2005)). The present invention now provides compositions polymerizing to much more favorable molded articles (see examples below).

It is particularly preferred that the surface of the molded article is modified. If the formulation contains, for example, methacrylic acid anhydride, the surface may easily be modified by means of aminolysis. Suitable substances thus becoming accessible (from the composition), or alternatively being attached, comprise peptides, which improve adhesion of osteoblasts or precursors of osteoblasts. These include peptides with RGD sequences, preferably peptides similar to collagen I or collagen IV. The surface is preferably modified by covalently attached proteins, peptides, amino acids or oligonucleotides.

It is particularly preferred that the molded article has a cellular or porous structure. Preferably, the cells have a wall thickness or pore size of 150 to 500 µm, especially around 200 µm. 200 µm corresponds to the average rod diameter of trabecular bones. Pore diameters of between 150 µm to 500 µm, especially 350 to 500 µm, are ideal for the adhesion of osteoblasts. This may be achieved by means of special molds in which the composition is polymerized, especially molds consisting of soluble material, wherein the molded article is obtained after dissolution of the mold in an appropriate solvent. On the other hand, such a structure may be created by rapid prototyping methods. In rapid prototyping methods, the solid molded article is built up by laying down layers of a solution or of a fluid composition of starting materials (the monomers), e.g. by slightly raising a lifting plate in a container holding the starting composition from the ground and irradiating the container from below with targeted light (with a special image for the respective layer to be polymerized) through its translucent (or UV transparent) bottom. By further raising the plate and irradiating, the next layer is built up, etc. The advantage of rapid prototyping methods is that molded articles with a desired geometry may be produced, which may be adapted exactly to the respective medical requirements, e.g. after removal of a bone tumor, the bone hole may be measured accurately (tomography) and a molded article that fits exactly into this hole may be produced by means of the imaging method.

Further possible methods for achieving cellular structures include (cf. L. J. Gibson, T. M. Freyman, I. V. Yannas, Cellular Materials as porous scaffolds for tissue engineering, Progress in Materials Science 46, 273-282 (2001)):
Salt leaching: NaCl particles and a polymer are mixed in solution. The solvent is evaporated, the polymer is heated above the melting point (better distribution of the particles), cooled, and placed in water, where the salt is dissolved. Here, a porosity of 20 to 93% is achievable, with a pore size in the range of 30 to 120 µm.
Foaming: $CO_2$ is dissolved under pressure (800 psi, 25° C.) in a polymer (composition), pressure is reduced, the gas expands and forms pores; typically 93% porosity, pore size 100 µm.
Fiber bonding: Polyglycolic acid (PGA) fibers are immersed in a solution of polylactic acid (PLA). The solvent is evaporated and the resulting network is heated above the melting point of PGA (network is fused), PLA is dissolved and a PGA network is obtained.
3D printing with Dorogen: PGA, PLA powder with NaCl, see above, 95% porosity, 100 µm pore size.

Preferably, the molded article is modified by bound proteins, peptides, amino acids, or oligonucleotides. Most preferably, these are bone morphogenic proteins (BMP), cytokines, growth factors (e.g. TGF-β, PTH), cell differentiation factors, collagens or collagen fragments, preferably BMPs and collagens, especially type II collagen. Examples for BMPs are known from the literature, especially BMP-1 (U.S. Pat. No. 5,108,922), BMP-2 and BMP-3 (U.S. Pat. No. 5,116,738 and U.S. Pat. No. 5,013,649), BMP-4 (U.S. Pat. No. 5,013,649), BMP-5 (U.S. Pat. No. 5,106,748), BMP-6 (U.S. Pat. No. 5,187,076) and BMP-7 (U.S. Pat. No. 5,108,753). Examples for nucleic acids or oligonucleotides that enhance bone growth are for instance disclosed in the EP 741 785. In medical applications, these proteins or oligonucleotides may also be administered separately. Preferably, the surface is modified by coating with hydroxyapatite.

In a further aspect, the present invention relates to molded articles for medical applications, especially as bone replacement substances or bone replacement parts, especially as implants. This is particularly advantageous for the treatment of bone damage, such as tumor-related bone cavities. In the body, the molded articles are degradable after a certain period of time, which, without being bound by any particular theory, is caused by slow penetration of water into the polymer.

In a related aspect, the invention also pertains to the use of an inventive molded article for producing implants for treating bone damage.

In the following examples, inventive compositions which may be used in a rapid prototyping method for producing mechanically stable bone replacement materials are shown and compared to prior art polymers.

EXAMPLE 1

Preparation of Gelatin Hydrolysate Methacrylamides GM1, GM2 and GM3

1 g (0.4 mmol) of gelatin hydrolysate (M<6000 g/mol, 0.63 mmol lysine/g) was dissolved in water while gently heating (not over 50° C.). After the addition of 1 g (6.7 mmol) methacrylic acid anhydride (MM), the mixture was stirred vigorously for 0.25 h (GM1), 4 h (GM2) and 5 h (GM3), respectively, in order to obtain different degrees of substitution. Excess methacrylic acid and methacrylic acid anhydride was then removed in vacuo. The average degree of substitution (DS) of methacryloyl-substituted lysine units was determined by NMR:
GM1: 1.03 g of yellow solid, DS=5%
GM2: 1.27 g of yellow oil, DS=47%
GM3: 1.18 of yellow oil, DS=52%
$^1$H-NMR (DMSO δ (ppm): 7.19 (m, aromatic-H); 5.39 (s, HCH=C); 5.62 (s, HCH=C); 4.70-0.75 (m, aliphatic-H); 1.5 (s, $CH_3$).

COMPARATIVE EXAMPLE 1

Preparation of Methacryloylated Oligoethylene Glycol/Lactic Acid Block Copolymers (E2-L20-M and E8-L20-M were prepared as described in A. Davis Kelly et al., Biomaterials 24(14), 2485-95 (2003))

|  | E2-L20-M | E8-L20-M |
| --- | --- | --- |
| D-L-Lactide | 10.0 g (69 mmol) | 10.0 g (69 mmol) |
| Diethylene glycol | 0.74 (7 mmol) | — |
| Polyethylene glycol 400 | — | 2.78 g (7 mmol) |
| Sn octoate | 94 mg (0.2 mmol) | 94 mg (0.2 mmol) |

-continued

|  | E2-L20-M | E8-L20-M |
|---|---|---|
| Triethylamine | 2.11 g (21 mmol) | 2.80 g (28 mmol) |
| Methacrylic acid chloride | 2.17 g (21 mmol) | 2.90 g (28 mmol) |
| $CH_2Cl_2$ abs. | 70 ml | 70 ml |

Diethylene glycol or polyethylene glycol 400 was stirred with $CaCl_2$ overnight and then collected by filtration. Methacrylic acid chloride was distilled freshly before use.

D,L-Lactide and the respective ethylene glycol were presented in a three-necked flask and heated to 130° C. When the D,L-lactide had melted, a catalyst was added, vacuum was applied, and the mixture was stirred at 130° C. for 6 h. After cooling, the oily solid was dissolved in anhydrous $CH_2Cl_2$, and triethylamine was added under $N_2$ atmosphere. The reaction mixture was cooled to 0° C., and 30 ml of methacrylic acid chloride, diluted with $CH_2Cl_2$, were slowly added dropwise. The reaction mixture was stirred further overnight at room temperature.

Finally, the salts were filtered off and the solvent was removed on a rotary evaporator. The residue was taken up in toluene, filtered again, and poured into cold PE. The product was reprecipitated again, then dissolved in $CH_2Cl_2$, and washed several times with a $NaHCO_3$ solution and brine, dried over $Na_2SO_4$, filtered, and evaporated.

E2-L20-M: 9.0 g of sticky solid (66% of theory)
$^1$H-NMR (DMSO): 6.18 (s, 2H, HCH=C); 5.62 (s, 2H, HCH=C); 5.13 (m, 20H, CH—CO); $\overline{4.25}$ (m, 4H, $CH_2$—O); $3.6\overline{5}$ (m, 4H, $CH_2$—O); 1.94 (s, 6H, $CH_3$—C=C); 1.58-1.46 (m, 60H, $CH_3$—C—O).

E8-L20-M: 4.5 g of yellow solid (33% of theory)
$^1$H-NMR (DMSO): 6.20 (s, 2H, HCH=C); 5.60 (s, 2H, HCH=C); 5.13 (m, 20H, CH—CO); $\overline{4.25}$ (m, 4H, $CH_2$—O); $3.7\overline{0}$-3.60 (m, 28H, $CH_2$—O); 1.97 (s, 6H, $CH_3$—C=C); 1.60-1.48 (m, 60H, $CH_3$—C—O).

Preparation of Test Pieces

Test pieces were produced for evaluating biocompatibility. Mixtures were prepared as shown in Table 1. The mixtures 1 to 4 were prepared as described in the literature. In all cases, the photoinitiator was 1% of a 1:1 molar mixture of campherquinone, dimethylaminobenzoic acid ethylester.

TABLE 1

Mixtures

| No. | Crosslinker | Comonomer | Filler | Solvent |
|---|---|---|---|---|
| 1 | 99% PEGM[3] | — | — | — |
| 2[1] | 6.7% PEGM[3] | — | 10% PEO | 82.3% PBS[7] |
| 3[2] | 99% E2-L20-M | — | — | — |
| 4[2] | 99% E8-L20-M | — | — | — |
| 5 | 30% GM1 | 50% AEEE[4] | 19% HA-T[6] | — |
| 6 | 30% GM2 | 50% AEEE[4] | 19% HA-T[6] | — |
| 7 | 30% GM2 | 50% DPA[5] | 19% HA-T[6] | — |
| 8 | 30% GM3 | 50% AEEE[4] | 19% HA-T[6] | — |
| 9 | 30% GM3 | 50% DPA[5] | 19% HA-T[6] | — |

[1]Dhariwala et al., Tissue Engineering 10, 1316-1322 (2004)
[2]Kristi S. Anseth et al., J. Polym. Sci. A 39, 683-692 (2001)
[3]PEG 400 dimethacrylate
[4]Acrylic acid (2-(2-ethoxy)ethoxy)ethyl ester (AEEE)
[5]Diisopropylacrylamide (DPA)
[6]1:1 mixture of hydroxyapatite and tricalcium phosphate (HA-T)
[7]PBS buffer: 10 mM sodium/potassium phosphate buffer pH 7.2, 0.8% NaCl and 0.02% KCl.

The mixtures were cast into a silicone mold and cured under nitrogen atmosphere on a UV unit. The test pieces obtained were extracted with organic solvents and water in an ultrasonic bath to remove residual monomers. The extracted polymer articles were sterilized with ultraviolet light.

Evaluation of Biocompatibility

For evaluating biocompatibility, osteoblast-like cells MC3T3-E1 were used. First, the adherent cells were detached from each other and from the bottom of the petri dish using pronase. Then they were mixed with freshly prepared culture medium and uniformly distributed on the individual test pieces in a multiwell plate. The culture medium consisted of commercially available Dulbecco's Modified Eagle's Medium (DMEM, which originally contains 1000 mg/l glucose and was combined with further glucose up to a concentration of 4500 mg/l), to which 10% FCS (fetal cow serum), 30 μg/ml gentamycin (broad-spectrum antibiotic), L-glutamine and ascorbic acid were added.

The multiwell plate with the cells was incubated at 37° C. Observation with a microscope showed whether the cells survived and were able to adhere. If living cells were present after 2 weeks of cultivation, they were fixed with a solution of 4% paraformaldehyde and 0.5% triton in PBS, washed several times with PBS buffer[7], and stained with a solution of 4,6-diamidino-2-phenylindole (DAPI, 5 μg/ml) in PBS buffer[7].

Biodegradability studies were conducted at 37° C. in PBS buffer at pH 7.0. The PBS buffer was changed every 12 hours during the first week, then every $3^{rd}$ day, to maintain a constant pH value. Samples were taken after 1, 3, 7, 21 and 30 days. The mechanical rigidity of the materials was obtained by determining the E-modulus by means of a dynamic mechanical analysis. The respective E-modulus values are shown in the following table:

| No. | Name | Microscope | DAPI staining | E-modulus (MPa) | E-modulus (MPa) (after 30 days) |
|---|---|---|---|---|---|
| 1 | PEG-dimethacrylate | ~ | -- | 0.92 | ** |
| 2 | PEG hydrogel | + | -- | 0.001 | ** |
| 3 | E2-L20-M | + | ++ | 440 | 80 |
| 4 | E8-L20-M | + | ~~ | 200 | 20 |
| 5 | GM1-AEEE* | | | | |
| 6 | GM2-AEEE | + | ++ | 1500 | 1350 |
| 7 | GM2-DPA | + | ++ | 2940 | 2620 |
| 8 | GM3-AEEE | + | ++ | 1650 | 1460 |
| 9 | GM3-DPA | + | ++ | 3130 | 2920 |

*mixture incompatible,
**test piece crumbled,
+living cells,
+partly living cells,
++numerous adhering cells,
~~some adhering cells,
-- no adhering cells As can be seen from the table, the inventive formulations 6 to 9 provided higher and durable rigidity values and at the same time excellent cell adherence compared to the known polymers 1 to 4 prepared according to prior art.

Molding

Cellular structures were produced by a molding technique. Wax molds (Solidscape Modelmaker) as well as organosoluble polymer molds were used. The monomer formulations were mixed with 1% benzoyl peroxide and 0.07 to 0.2% of 4-(dimethylamino)benzoic acid ethylester (DMAB), filled into the respective mold and cured at 45 to 75° C. for several hours. The wax mold was removed by dissolution in ethanol, the organosoluble mold was removed in a 1:4 mixture of n-butylamine and tetrahydrofuran.

The invention claimed is:

1. A method for producing a polymerizate, said method comprising:
   A) preparing a polymerization-curable composition by mixing 10 to 80% by weight of component a) with 10 to 50% by weight of component b)
   wherein
   component a) is a reactive diluent based on acrylic acid or methacrylic acid derivatives, and component b) is a liquid gelatin hydrolysate or a gelatin hydrolysate soluble in the reactive diluent, said liquid gelatin hydrolysate or gelatin hydrolysate soluble in the reactive diluent substituted with a radical of the formula

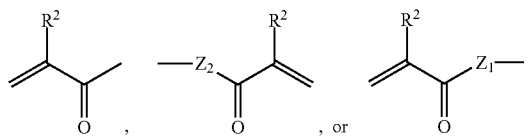

wherein
   $R^2$ is H or —$CH_3$;
   $Z_1$ is —O—$(CH_2)_x$—CO—, —O—$(CH_2$—$CH_2$—O$)_x$—$CH_2$—CO—, —O—$(CH_2$—$CH_2$—O$)_x$—CO—$CH_2$—$CH_2$—, —O—$(CH_2$—$CH_2$—O$)_x$—OC—CH=CH—CO—, —O—$CH_2$—CH(OH)—$CH_2$—, or —O—$(CH_2$—$CH_2$—O$)_x$—$CH_2$—CH(OH)—$CH_2$—;
   $Z_2$ is —O—$(CH_2)_x$—O—, —O—$(CH_2$—$CH_2$—O$)_x$—, —O—$CH_2$—CH(OH)—$CH_2$—O—, or —O—$CH_2$—CH(OH)—$CH_2$—O—$(CH_2$—$CH_2$—O$)_x$—;
   x is 1 to 20;
   said liquid gelatin hydrolysate or gelatin hydrolysate soluble in the reactive diluent having a molecular weight of up to 10,000 Da; and
   B) polymerizing the polymerization-curable composition, in a mold or in layers, into a polymerizate having an E-modulus of more than 1,000 MPa.

2. The method of claim 1, wherein in step B), the polymerization-curable composition is polymerized by radiation with ultraviolet or visible light.

3. The method according to claim 1, wherein the component a) is acrylic acid (2-(2-ethoxy)ethoxy)ethyl ester, diisopropylacrylamide, diisobutylacrylamide, acrylic acid 2-(butylcarbamoyloxy)ethyl ester, hydroxyethylmethacrylate, polyethylene glycol diacrylate, trimethylolpropane triacrylate, or a mixture thereof.

4. The method according to claim 1, wherein the component b) comprises a methacryloylated gelatin hydrolysate.

5. The method according to claim 1, wherein the component b) comprises peptides comprising the sequence arginine-glycine-aspartic acid (RGD).

6. The method according to claim 1, wherein 2 hydroxy-1-[4-(2-hydroxyethoxy)phenyl]-2-methyl-1-propanone or phenyl-bis(2,4,6-trimethylbenzoyl)phosphine oxide is added to the polymerization-curable composition as an initiator.

7. The method according to claim 1, wherein campherquinone is added to the polymerization-curable composition as an initiator and one or more of dimethylaniline, triethanolamine or methyl diethanolamine is added to said polymerization-curable composition as a co-initiator.

8. The method according to claim 1, wherein hydroxyapatite, tricalcium phosphate, bone meal, or keratin fibers is added to the polymerization-curable composition as filler.

9. The method according to claim 1, wherein the components of the composition are dissolved in organic solvents comprising a water content of <10%.

10. A molded article prepared according to claim 1, wherein the molded article has a cellular structure having a pore diameter between 150 μm and 500 μm.

11. A molded article prepared according to claim 1, wherein a surface of the molded article comprises a coating of hydroxyapatite.

12. A molded article prepared according to claim 1, wherein a surface of the molded article comprises covalently attached proteins, peptides, amino acids, or oligonucleotides.

13. The molded article according to claim 12, wherein the proteins are selected from the group consisting of bone morphogenic proteins (BMP), cytokines, growth factors and cell differentiation factors, collagens, and collagen fragments.

14. The method according to claim 1, wherein the components of the polymerization-curable composition are dissolved in organic solvents comprising a water content of less than about 1%.

15. The method according to claim 1, wherein the components of the polymerization-curable composition are dissolved in organic solvents comprising a water content of less than about 0.1%.

16. The method of claim 1, wherein the polymerizate obtained in step B) has an E-modulus of more than 1,500 MPa.

17. The method of claim 16, wherein the polymerizate has an E-modulus of more than 2,000 MPa.

18. The method of claim 17, wherein the polymerizate has an E-modulus of more than 5,000 MPa.

19. The method of claim 18, wherein the polymerizate has an E-modulus of more than 10,000 MPa.

* * * * *